United States Patent [19]

Goodling et al.

[11] E Re. 31,202

[45] Reissued Apr. 12, 1983

[54] POULTRY BEAK REMOVER

[75] Inventors: John S. Goodling; Gayner R. McDaniel, both of Auburn, Ala.; Richard A. Steadham, Texas City, Tex.

[73] Assignee: Auburn Research Foundation, Auburn, Ala.

[21] Appl. No.: 63,355

[22] Filed: Aug. 2, 1979

Related U.S. Patent Documents

Reissue of:

[64] Patent No.: 4,040,425
Issued: Jun. 9, 1977
Appl. No.: 646,924
Filed: Jan. 6, 1976

[51] Int. Cl.[3] ..... A61B 17/36

[52] U.S. Cl. ..... 128/303.14; 219/384

[58] Field of Search ..... 128/303.1, 303.13, 303.14, 128/303.17, 303.18, 305; 219/384

[56] References Cited

U.S. PATENT DOCUMENTS

| | | | |
|---|---|---|---|
| 2,792,004 | 5/1957 | Sandy | 128/303.1 |
| 3,302,645 | 2/1967 | Lockmiller | 128/305 X |
| 3,463,155 | 8/1969 | Lyon | 128/303.1 |
| 3,570,487 | 3/1971 | Reynolds | 128/303.1 |
| 3,614,382 | 10/1971 | Politzer | 128/303.14 X |
| 3,625,218 | 12/1971 | Valinoti, Jr. | 128/303.14 |
| 3,812,857 | 5/1974 | Lyon | 128/303.1 |

*Primary Examiner*—Lee S. Cohen

[57] ABSTRACT

A poultry beak remover for debeaking fowl includes a housing having a pair of spaced apart electrodes supported therein and a beak receiving aperture therein for insertion of the beak of the fowl into the housing into proximity with the electrodes, and electrical circuitry connected with the electrodes for discharging a spark to burn the beak of the fowl and thus effect removal of a desired portion thereof.

15 Claims, 14 Drawing Figures

FIG.1.
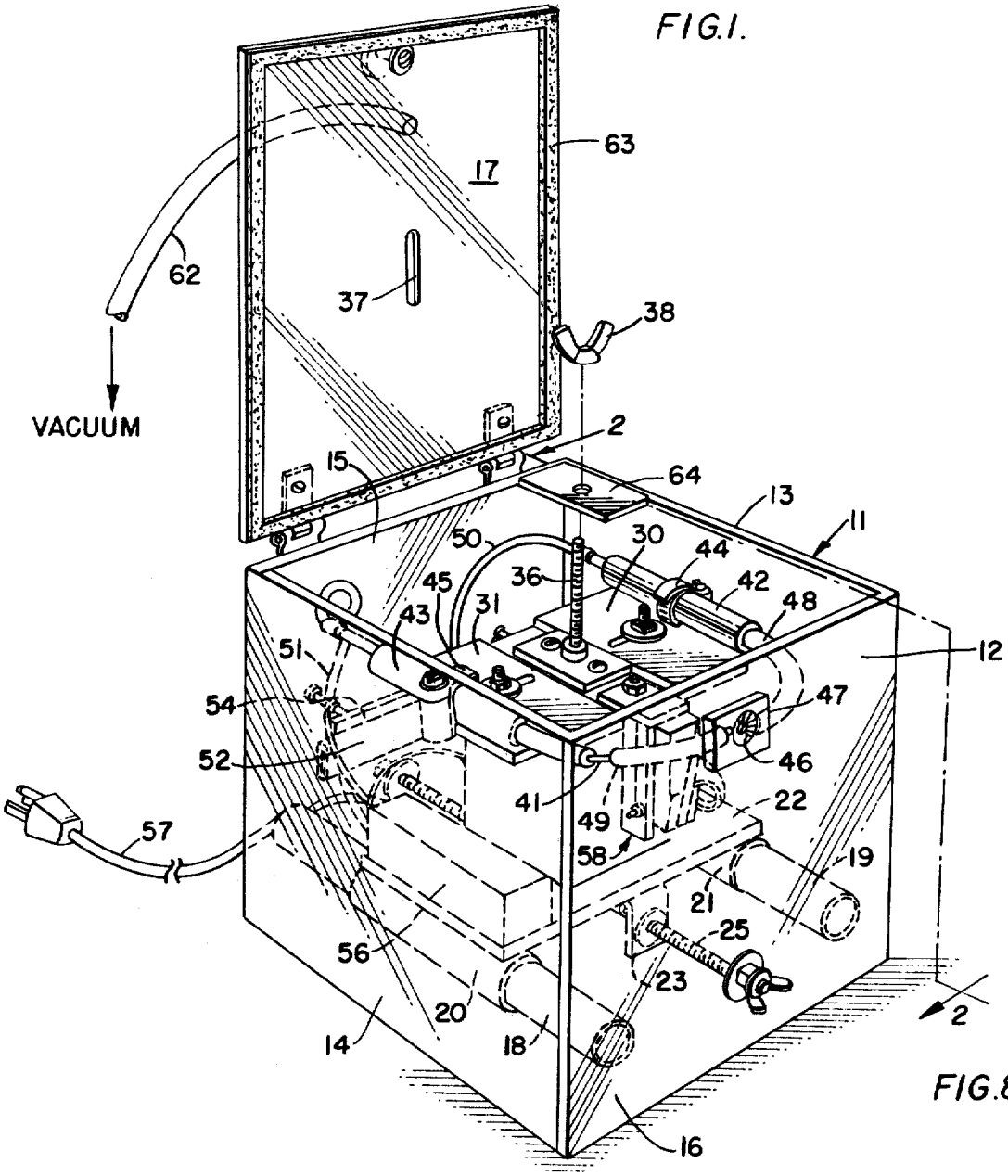
FIG.8.
FIG.6.
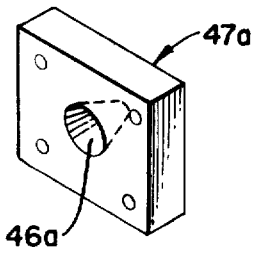
FIG.7.
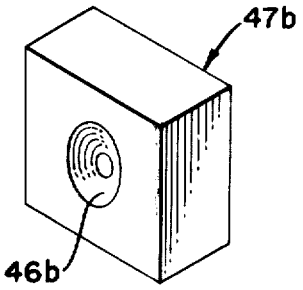
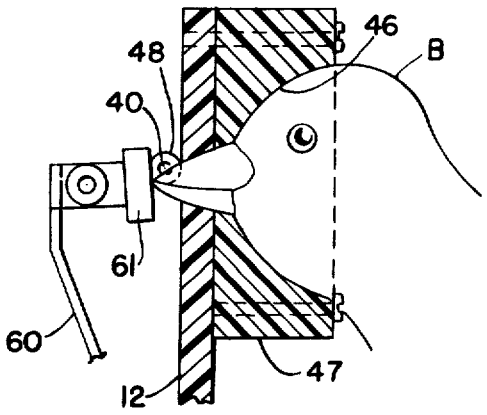

12V POWER SUPPLY

START
(58) 78
A
2
S
R
Q
12V
+12V
Q22
Q23
Q19
Q20
B
T1
T2
T3
7V
+7VDC
REG
C1
C2
C3
C4
R1
R2

107
1mfd
470K
108
Q12
77
Q11
Q10
106
Q9
Q8
OR GATE
105
Q7
Q6
104
Q5
Q4
Q3
72
101
2μf
102
100
103
82
2
Q
+7V
Q1
Q2
81
S
+7VDC
A
+7VDC REG.
RDY
+12V
109
110
111
Q13
Q14
Q15
CHG
ARC
12V
R2
83
Q18
Q31
Q30
+12V
Y+7V
Q17
Q16
NAND GATE
PUSH BUTTON TURN ON
VAR TIME
ARC
FIXED TIME
CHARGE

POULTRY BEAK REMOVER

Matter enclosed in heavy brackets [ ] appears in the original patent but forms no part of this reissue specification; matter printed in italics indicates the additions made by reissue.

BACKGROUND OF THE INVENTION

This invention relates in general to apparatus for removing a desired portion of the beak of birds, and in particular, from poultry.

It is a curious habit of birds such as chickens and turkeys and the like to peck at other birds or to peck at spots such as dirt or blood and the like appearing on individual birds. Accordingly, such pecking can result in damage or destruction of large numbers of birds if the beaks of the birds are left intact.

Many devices are known in the prior art for removing a portion or all of the beak of birds such as chickens and turkeys and/or game birds and the like for preventing pecking and egg eating and other undesirable characteristic actions of the birds. Such devices typically remove a portion of the upper mandible of the beak, leaving substantially intact the lower mandible, such as to not hinder the feeding capability of the bird, but yet at the same time to shorten and dull the beak of the bird to prevent it from harming other birds. Moreover, it is desirable with such devices that in conjunction with removal of a portion of the beak the tissue is charred to prevent hemorrhage of the shortened beak. Some such prior art devices are exemplified in U.S. Pat. Nos. 2,501,283 and 3,390,679, for example, in which an apparatus for burning the upper mandible of a beak and an apparatus for cutting the beak are shown, respectively.

However, all such prior art devices require either operator skill to properly manipulate the birds or are relatively slow in operation, thus severely reducing the number of birds which can be debeaked during a given time period. Accordingly, with prior art devices, a very large number of birds are improperly debeaked, with the result that they are either prevented from feeding properly or they remain enabled to peck other birds and the like. Moreover, improper debeaking results in the added biological stress of a large number of birds, with a resultant increase in the cost to the consumer of the remaining birds.

SUMMARY OF THE INVENTION

The present invention provides a poultry beak remover for removing a desired portion of the beak of poultry and game birds and the like to prevent the birds from harming one another throughout their lives. In the poultry industry it is common to debeak chickens when they are approximately 3 days old, and the number of chickens debeaked is in the millions. For example, upwards of 100,000 chickens may be debeaked at a given hatchery on a given day.

The poultry beak remover of the present invention includes a pair of spaced apart electrodes positioned in proximity to a beak receiving aperture through which the beak of the poultry is inserted, and means is provided for discharging a spark across the electrodes to burn a portion of the upper mandible of the beak by means of the spark discharge to thus effect removal of the beak. The spark discharge is extremely rapid and automatically cauterizes the burned portion of the beak to prevent hemorrhage, and the arrangement of aperture, electrodes and spark discharge control means is such that the operator does not require any skill to use the poultry beak remover, and except for placing the chick with its beak in the aperture, the operation of the device is automatic and accurate. For example, if 3 day old chicks are being debeaked with the device of the present invention, an appropriately sized aperture is provided and the electrodes are positioned relative to the hole such that simply by inserting the beak of the chick through the aperture, the upper mandible thereof is positioned relative to the electrodes, such that the upper mandible is burned at a desired portion and the forward end of the beak engages means to effect spark discharge across the electrodes for burning of the beak. Therefore, with the present invention birds can be debeaked in only about one-third the time required to debeak birds with prior art devices.

More particularly, the device of the invention comprises a preformed mold of a portion of or all of the birds head or beak, behind which are located two electrodes separated enough for the beak to be inserted between them. Upon insertion of the beak, a switch is actuated, allowing an electric potential to form across the electrodes of sufficient strength to cause a spark to be created across the electrodes in the vicinity of the bird's beak. The placement of the beak and the total time of spark emission and intensity of the spark are adjusted to have the effect of destroying whatever portion of the beak tissue is desired or necessary to cause the appropriate effect. Debeaking of the bird is thus caused automatically when the switch is actuated upon placement of the bird's head in the proper position. An electronically controlled circuit is used to provide proper timing, voltage and current to the electrodes, and the essential part of the electrical circuit is a charging and discharging capacitor across the primary side of a coil using either ac or dc electrical power.

The beak aperture or mask of the bird's face and/or beak is readily replaceable to accommodate birds of different size and/or age, and the position of the electrodes relative to the beak aperture is adjustable in three directions, so as to accommodate poultry of any size or to effect burning of a desired portion of the beak.

OBJECTS OF THE INVENTION

Accordingly, it is an object of this invention to provide a poultry beak remover which utilizes a spark discharge to burn a portion of a bird's beak to effect removal of a desired portion thereof.

Another object of the invention is to provide a poultry beak remover for burning a portion of a bird's beak to effect removal thereof, wherein operation of the beak remover is automatic and accurate, and wherein adjustments of the beak burning means are provided in at least three directions to accommodate birds of different size.

A still further object of the invention is to provide a poultry beak remover wherein a beak aperture is provided through which the beak of a bird is inserted, and a pair of spaced electrodes are positioned in proximity with the aperture between which the upper mandible of the beak is positioned when inserted through the aperture, and switch means is positioned to be engaged by the forward portion of the beak as it is extended into proper position in the aperture, to thereby effect spark discharge across the electrodes to burn a desired portion of the beak and effect removal of a desired portion thereof.

A further object of the invention is to provide a poultry beak remover having means for effecting a spark discharge to burn a specified portion of the beak, and including means of innoculating the bird while it is being debeaked.

Yet another object of the invention is to provide a poultry beak remover which burns a specified portion of the beak by means of a spark discharge, and wherein an electronic control circuit is connected to control the spark discharge and includes means for effecting an initial discharge of a high voltage spark to ionize the air between a pair of spaced electrodes and subsequently to reduce the spark voltage to a low, energy efficient level for burning the beak of the bird.

BRIEF DESCRIPTION OF THE DRAWINGS

FIG. 1 is a perspective view of a poultry beak remover in accordance with the present invention, showing the cover thereof in open position.

FIG. 6 is a perspective view of a first mask in accordance with the invention, having a beak receiving aperture therethrough.

FIG. 7 is a perspective view of a second form of mask or beak receiving aperture according to the invention.

FIG. 8 is a somewhat schematic, fragmentary view in section showing the operative relationship of a bird's head and beak and the mask and beak receiving aperture, with reference to the spaced electrodes and the switch actuating means.

DETAILED DESCRIPTION OF THE PREFERRED EMBODIMENTS

Figure 2:
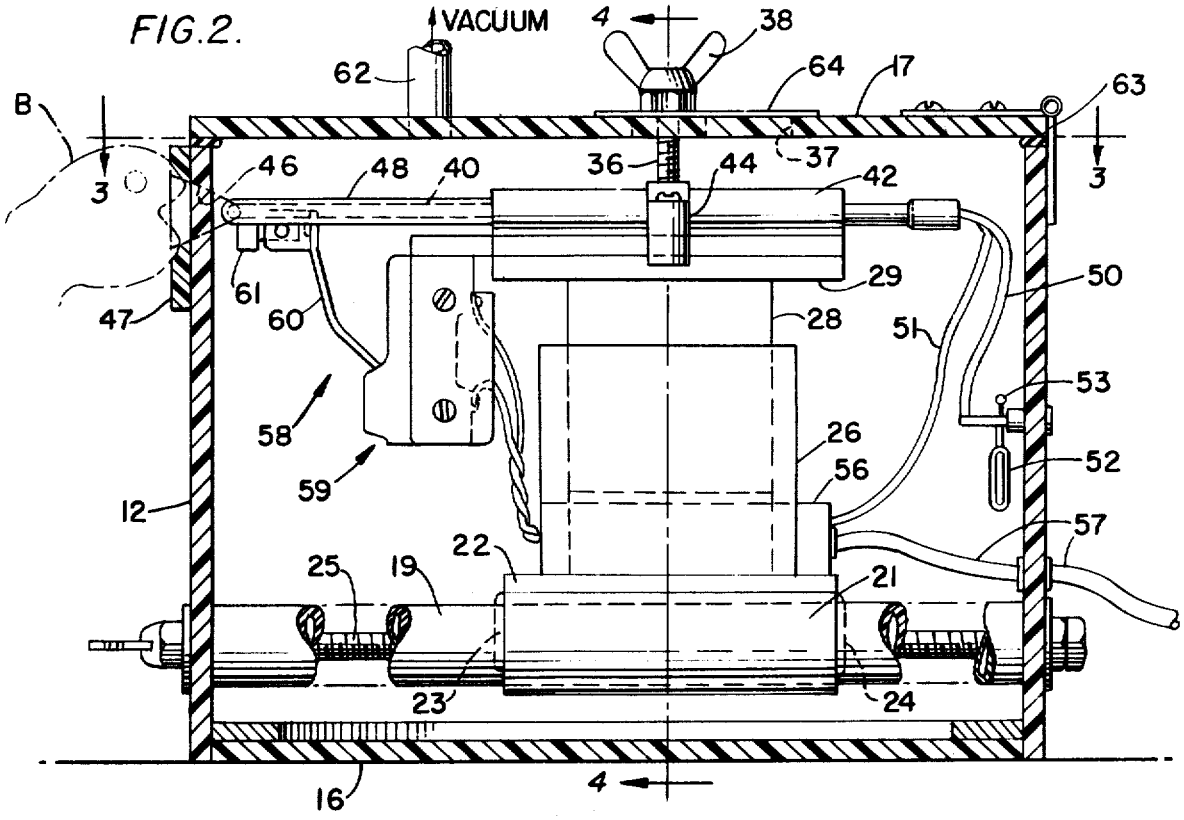
FIG. 2 is an enlarged view in section taken along line 2—2 in FIG. 1.
Figure 3:
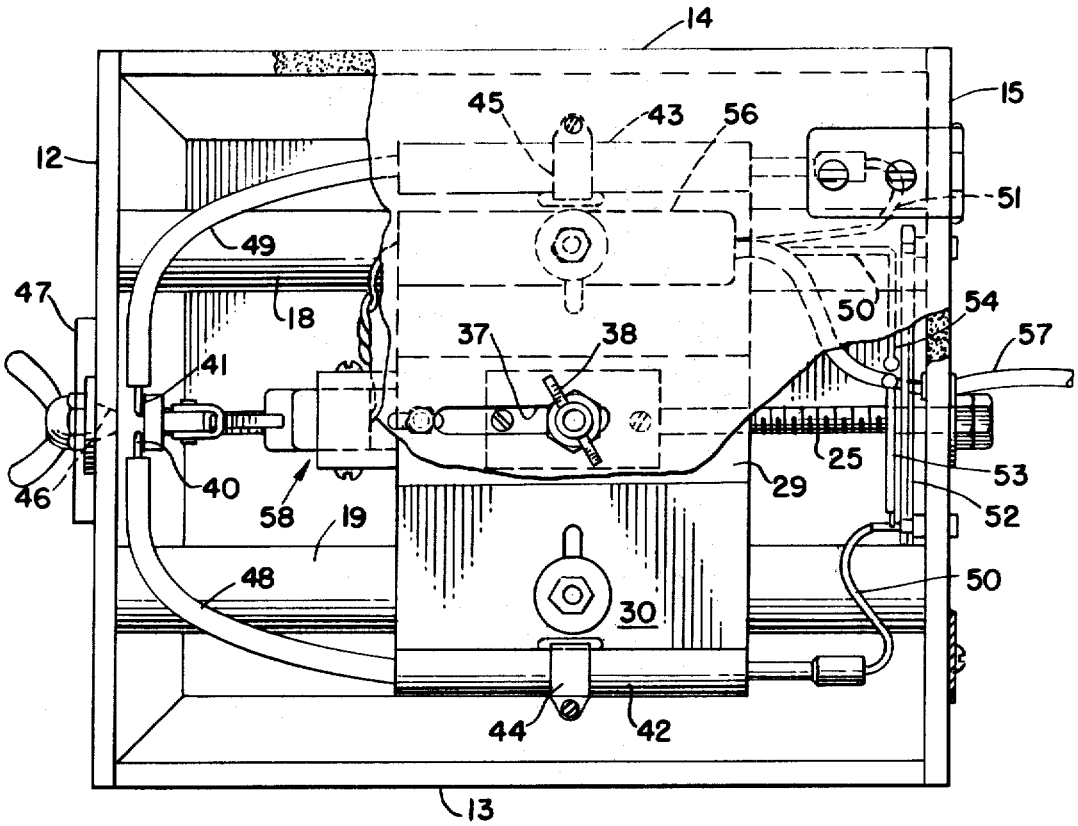
FIG. 3 is a plan view of the beak remover taken along line 3—3 in FIG. 2.

In the drawings, wherein like reference numerals indicate like parts throughout the several views, the beak remover is indicated generally at 10, and includes a housing 11 made of a non-conducting material, such as plastic or the like, and having a front wall 12, opposite side walls 13 and 14, a back wall 15, a bottom wall 16, and a removable or hinged cover or top wall 17.

A pair of substantially parallel, elongate guide members 18 and 19, such as tubes or the like, are secured at their opposite ends to the front and back walls 12 and 15, respectively, in inwardly spaced relationship from the side walls 13 and 14 and upwardly spaced relationship from the bottom wall 16.

A pair of guide sleeves 20 and 21 are slidably received on the guide members or tubes 18 and 19 for sliding movement therealong, and a support plate or base 22 is supported on top of the guide sleeves 20 and 21 in spanning relationship thereto and is secured to the guide sleeves by any suitable means, such as adhesive or the like, or the plate 22 may be formed integrally with the guide sleeves 20 and 21, if desired.

A pair of downwardly extending brackets 23 and 24 are suitably affixed to the plate 22 at the front and rear edges thereof substantially intermediate the opposite side edges of the plate, and an elongate, threaded adjusting rod 25 extends through aligned openings in the front and back walls 12 and 15 and through mating threaded openings in the brackets 23 and 24. The threaded rod 25 is held against axial movement relative to the housing 11, and when the rod 25 is rotated, the threaded engagement thereof with the brackets 23 and 24 causes the brackets and thus the plate 22 and guide sleeves 20 and 21 to move longitudinally of the guide members 18 and 19.

An upstanding, tubular mounting sleeve 26 is suitably secured on the upper surface of support plate 22 substantially centrally located relative thereto, and has an open upper end 27. An electrode support and guide member 28 is telescopically received in the mounting sleeve 26 for up and down sliding movement relative thereto. An electrode support plate 29 is suitably affixed to the upper end of support and guide member 28, and pair of slotted electrode support brackets 30 and 31 are laterally adjustably secured to the top surface of electrode support plate 29 by means of bolts and screws and the like 32 and 33 and associated nuts 34 and 35. A threaded rod 36 is secured at its lower end to the support plate 22 and extends coaxially upwardly through the mounting sleeve 26 and supporting guide member 28 and through the center of electrode support plate 29, whereat a threaded portion of rod 36 is engaged with mating threads in the electrode support plate 29. The upper end of the rod 36 extends through an aligned, slotted opening 37 in the cover 17, and a wing nut 38 or the like is secured thereon, whereby the rod may be rotated, and upon rotation of the rod 36, the electrode support plate 29 and support and guide member 28 are caused to move up and down relative to the housing and mounting sleeve 26. A spring 39 is engaged between the support or base plate 22 and the electrode support plate 29 for resiliently urging these plates apart to maintain the relatively movable parts in snug interengagement and prevent excessive looseness thereof. This, in turn, enables more accurate adjustment of the relatively movable parts and the electrodes carried thereby.

A pair of electrodes 40 and 41, surrounded by an insulating housing 42 and 43, respectively, are adjustably and removably clamped to the electrode mounting brackets 30 and 31 by means of hose clamps or other suitable fastening means or the like 44 and 45, respectively. The electrodes 40 and 41 extend forwardly from the insulating sleeves 42 and 43 and are curved inwardly into spaced apart relationship adjacent the inner surface of front wall 12 in alignment with a beak receiving aperture 46 therethrough.

A suitable mask 47, configured to fit a bird B of predetermined age, type and size, is removably secured to the front wall 12 in registry with the beak receiving aperture 46, whereby the selected bird may be positioned with its head or face in the mask 47 and its beak extended through the aperture 46 and the beak will be positioned properly with reference to the electrodes 40 and 41, as seen, for example, in FIG. 8.

The forwardly extending, curved portions of electrodes 40 and 41 are covered with a suitable insulating material 48 and 49, respectively, except for the tip portions of the electrodes adjacent the beak receiving aperture 46. The electrodes may be of any suitable type, and are connected via wires 50 and 51, respectively, with a suitable source of power.

Figure 4:
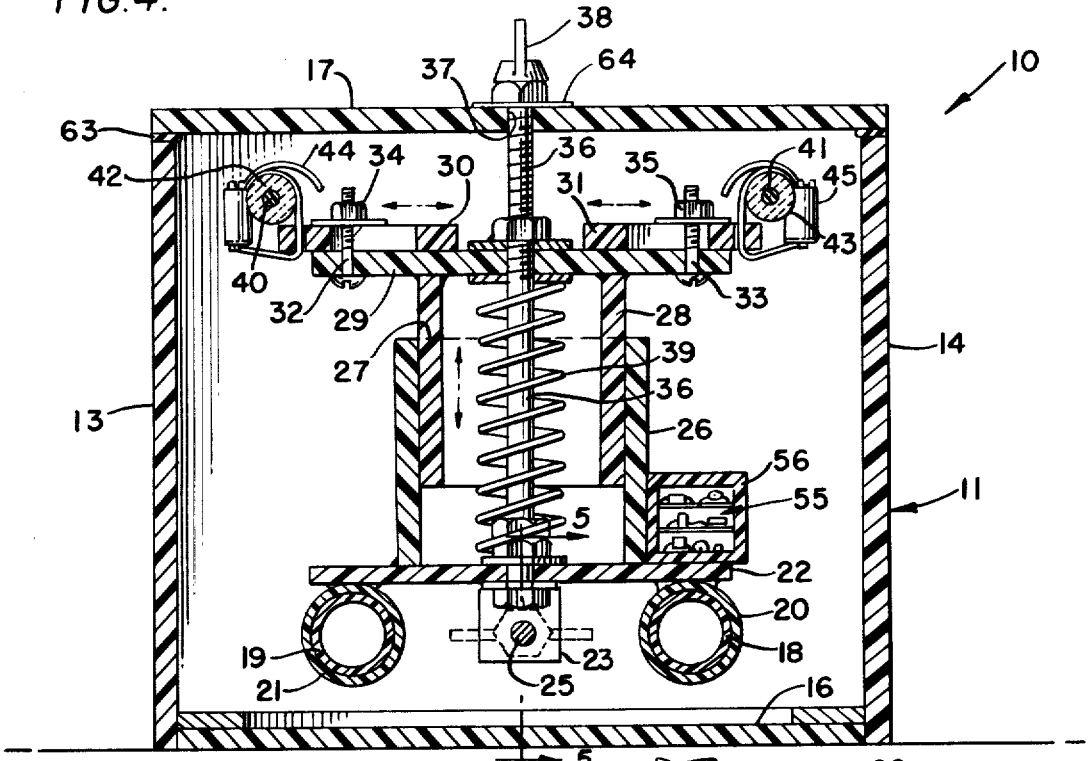
FIG. 4 is a vertical sectional view taken along line 4—4 in FIG. 2.
Figure 5:
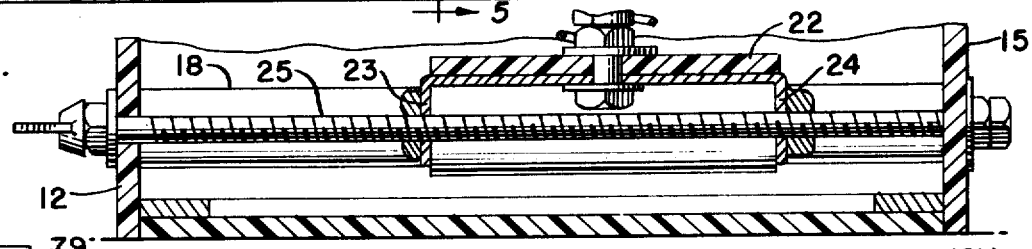
FIG. 5 is a fragmentary view in section taken along line 5—5 in FIG. 4.
Figure 9:
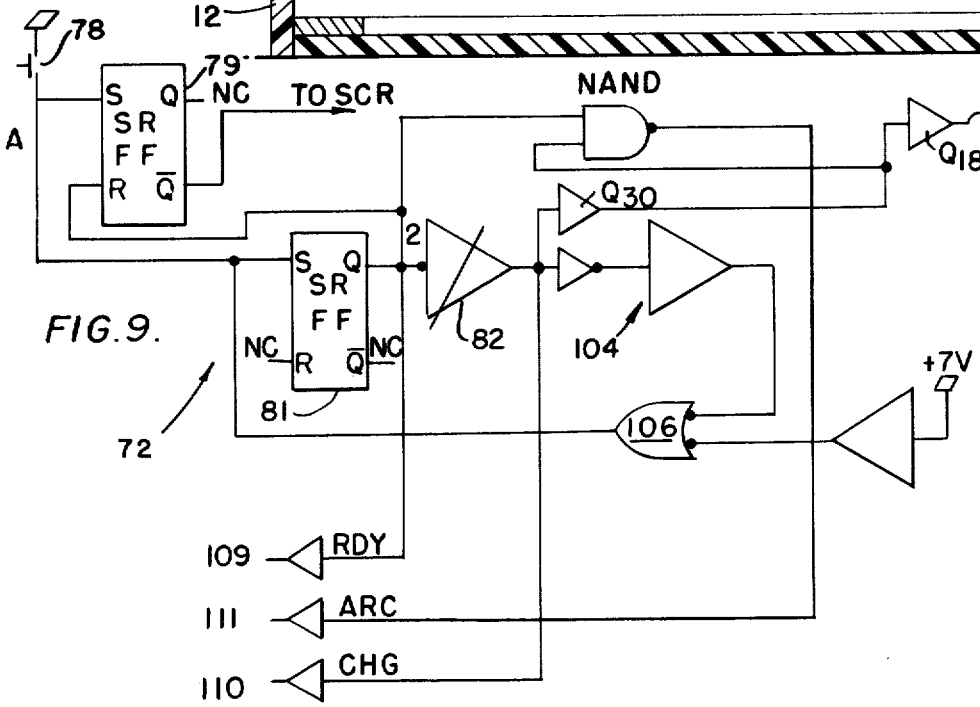
FIG. 9 is a block diagram of the circuitry used in controlling the spark discharge.
Figures 10, 10A, 11:
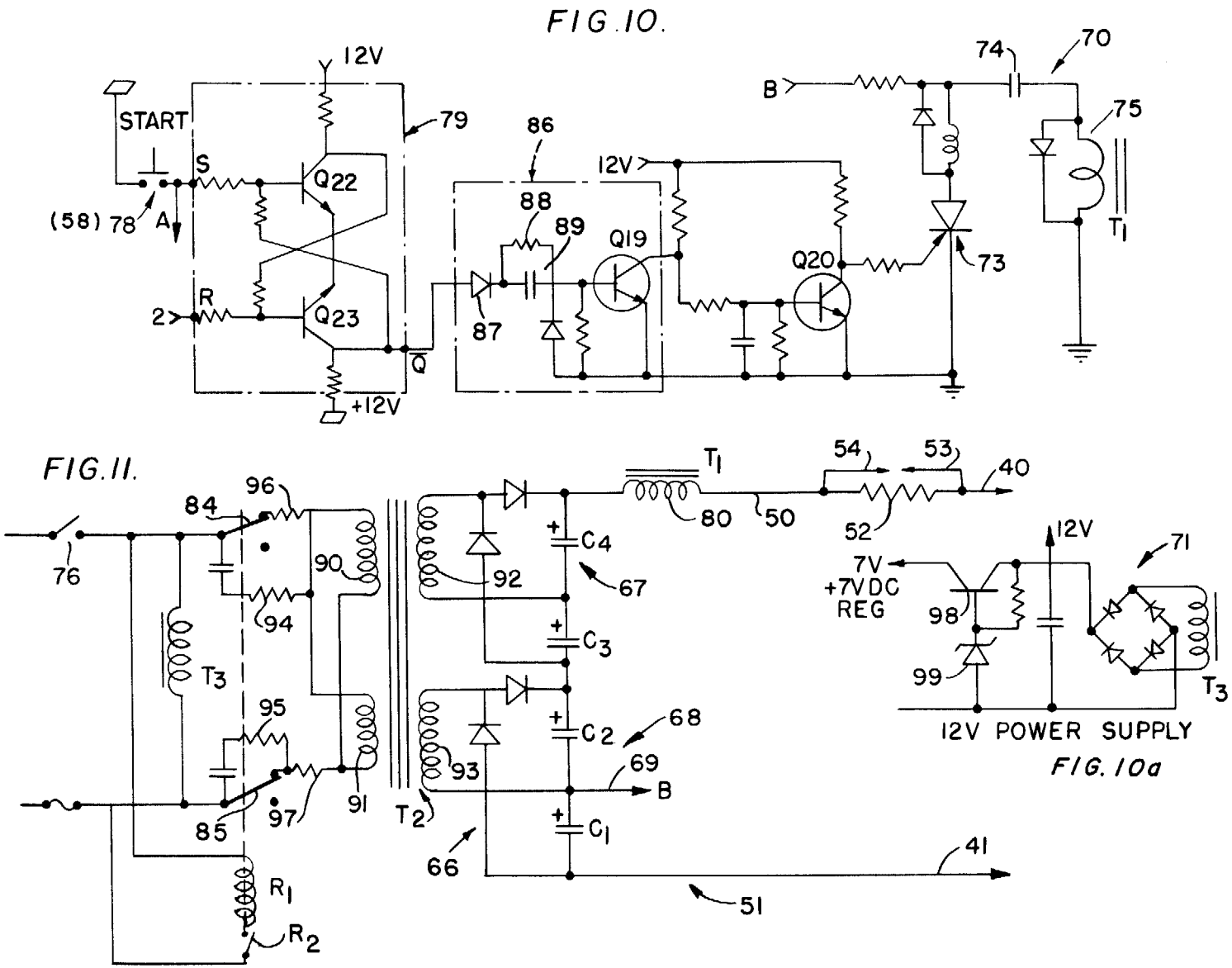
FIG. 10 is a schematic diagram of the spark discharge circuit.
FIG. 10a is a schematic diagram of the logic power supply.
FIG. 11 is a schematic diagram of the high voltage power supply.

As seen in the drawings, particularly FIG. 11, one of the electrodes, as for example, electrode 40, has its power supply wire 50 connected through a resistor element 52 and a pair of spark gap elements 53 and 54 connected in parallel with the resistor 52 between the ends of the electrode power supply wire 50. The wires 50 and 51 are then connected with suitable electrical circuit means an circuitry 55 (FIG. 4) in a housing 56 carried, for example, by the base plate 22. A main power supply cord 57 extends from a suitable source of power, such as 110 volt ac power, to the electrical circuitry 55 in the housing 56.

A switch means 58 for controlling the spark discharge includes a microswitch element 59 of conventional construction suitably secured to the forward edge portion of plate 29, and having an actuating arm 60 extending upwardly to an abutment plate 61 in proximity with the electrode tips and beak receiving aperture 46, whereby upon proper insertion of the beak of a bird B, the abutment plate 61 is engaged by the beak, moving the arm 60 and operating the switch 59 to initiate a burn cycle.

Preferably, the interior of the housing 11 is subjected to a partial vacuum through a vacuum line 62 to remove noxious odors from the housing and also to aid in properly positioning and holding the beak relative to the beak receiving aperture 46 and electrodes 40 and 41. The housing is suitably sealed to maintain the integrity of the vacuum, and for example, a gasket 63 is carried by the hinged cover 17 for sealing against the upper edge of the front, back and side walls. Also, a suitable sealing plate 64 of desired material is, or may be, provided in association with the rod 36 and slotted opening 37 for sealing the opening 37.

In FIGS. 6 and 7, alternate types of masks or beak aperture plates 47a and 47b are shown, having different size and shape beak receiving apertures 46a and 46b therethrough for receiving birds of different age, size and/or type.

The control circuit for controlling the initiation, time of discharge and intensity of the spark discharge is comprised of several sections, including a high voltage power supply 66 (FIG. 11) of 1600 volts, 500 watts, obtained from two voltage doublers 67 and 68 connected with a 110 volt ac power source. The high voltage power supply 66 has a tap 69 at 400 volts for the SCR controlled spark discharge circuit 70. A 12 volt power supply 71 (FIG. 10a) is connected to the transistor logic circuitry 72 to run the logic circuitry. The high voltage spark that is needed to jump the gap between the electrodes 40 and 41 to ionize the path for the 1600 volt beak burning arc is generated with the SCR switched or capacitor discharge ignition type system 70. The capacitor discharge, high voltage spark generator 70 utilizes a high voltage, high current SCR 73 to discharge a capacitor 74 across the primary 75 of a step-up transformer T1 to generate approximately 40,000 volts.

In operation, the transistor logic network 72 generates the sequence of events or timing of the spark discharge. Upon turning the unit on with on-off switch 76 (FIG. 11), there is a time delay lockout 77 (FIG. 12) operative for approximately 200 milliseconds that inhibits the spark pulse or any spurious pulses from initiating spark discharge. After this time, the unit is in a ready state, and upon actuating the spark actuation switch 78 (58) (FIG. 10), a bounce eliminator flip-flop 79 (FIG. 10) is set. The output of this flip-flop 79 sends a signal to a pair of driver transistors Q19 and Q20 (FIG. 10), with filters, to shape the turnon time and drive the gate of the SCR 73 to turn it on. When the SCR 73 is turned on, it discharges the 2 microfarad capacitor 74 that has been charged to 400 volts from the 400 volt tap 69 of the 1600 volt power supply 66, and the secondary 80 of the transformer T1 that this capacitor discharges across generates 40,000 volts to ionize the air in the gap between the electrodes 40 and 41 to start the burn arc. Also, from the spark actuation switch 78 power is supplied to a second logic flip-flop 81 (FIG. 12), which starts the chain of events in the logic sequence. This, in turn, sends a signal to an emitter-coupled transistor timer 82 with an RC time constant to the input. This timer controls the duration of the burning arc. Upon completion of this time constant, the timer sends a signal to a second switch 83, which shuts down the high voltage power supply by means of a 110 volt relay R1 (FIG. 11) which operates to open switches 84 and 85. Relay R1 is controlled by a smaller 12 volt relay R2 operated from the logic circuit. When relays R1 and R2 are de-energized at the end of the prescribed time, switches 84 and 85 return to their original position, thereby connecting the 110 volt supply to the high voltage power supply. Also, this resets the SCR. Upon completion of the above-described time delay, the unit is back in a ready state. This additional time delay enables the power supply to charge its capacitor bank up, thus completing one cycle of operation.

Referring now to FIG. 10, the set-reset flip-flop 79 comprises two transistors Q22, Q23, with the start input connected with the set side S and a reset connected with the reset side R. When the start switch 78 is actuated by engaging abutment plate 61, the flip-flop 79 is switched to the set position, which causes the reset side to go high coupling with a pulse-shaping network 86 through a diode 87 into a resistor 88 and capacitor 89 feeding the base of transistor Q19. The pulse shaping network applies the proper time for the SCR 73. The output of transistor Q19 is dc coupled to a driver transistor Q20, which is held on all the time and is turned off to allow a positive level to go to the gate of the SCR 73. The SCR then switches on and causes the two microfarad 400 volt capacitor 74 that has been previously charged from the 400 volt tap of high voltage power supply to discharge abruptly across the primary 75 of the high voltage spark induction transformer.

In FIG. 11 the 1600 volt, 500 watt high voltage power supply 66 includes a transformer T2 connected across the power supply leads. The transformer T2 includes a pair of primary windings 90 and 91 and high voltage secondary windings 92 and 93. The power supply is turned on by 117 volt ac coiled relay R1, which operates the normally closed switches 84 and 85 connected in the primary leads to the high voltage power supply. Spark suppressor resistors 94 and 95 are connected across the relay contacts. In series with the transformer leads are surge current limiting resistors 96 and 97. The voltage doubler circuits 67 and 68 are in series on the high voltage secondary windings, thus giving 1600 volts dc from the four series connected, 400 volt capacitors C1, C2, C3 and C4. The tap 69 at the first 400 volt capacitor C1 is used for charging the capacitor discharge capacitor 74 in the spark discharge circuit. The secondary winding 80 of the high voltage ignition transformer T1 is in the positive lead of the power supply, and as previously explained, generates the 40,000 volts for ionization, thus enabling the relative low 1600 volts to complete the spark burning of the beak. Also, the current limiting resistor 52 is connected in series therewith to limit the current of the high voltage power supply through the arc so as not to drop the voltage to extinguish the arc. The spark gap 53, 54 is shunted across the current limiting resistor 52 and is adjusted so that the high voltage ignition spark will jump the gap and not be quenched by the current limiting resistor.

The 12 volt logic power supply 71 in FIG. 10a is a full wave, bridged, 12 volt dc power supply, with a series pass transistor 98 controlled by a 7 volt zener diode 99 to give a regulated 7 volts, and obtains power from transformer T3.

Figures 12, 13:
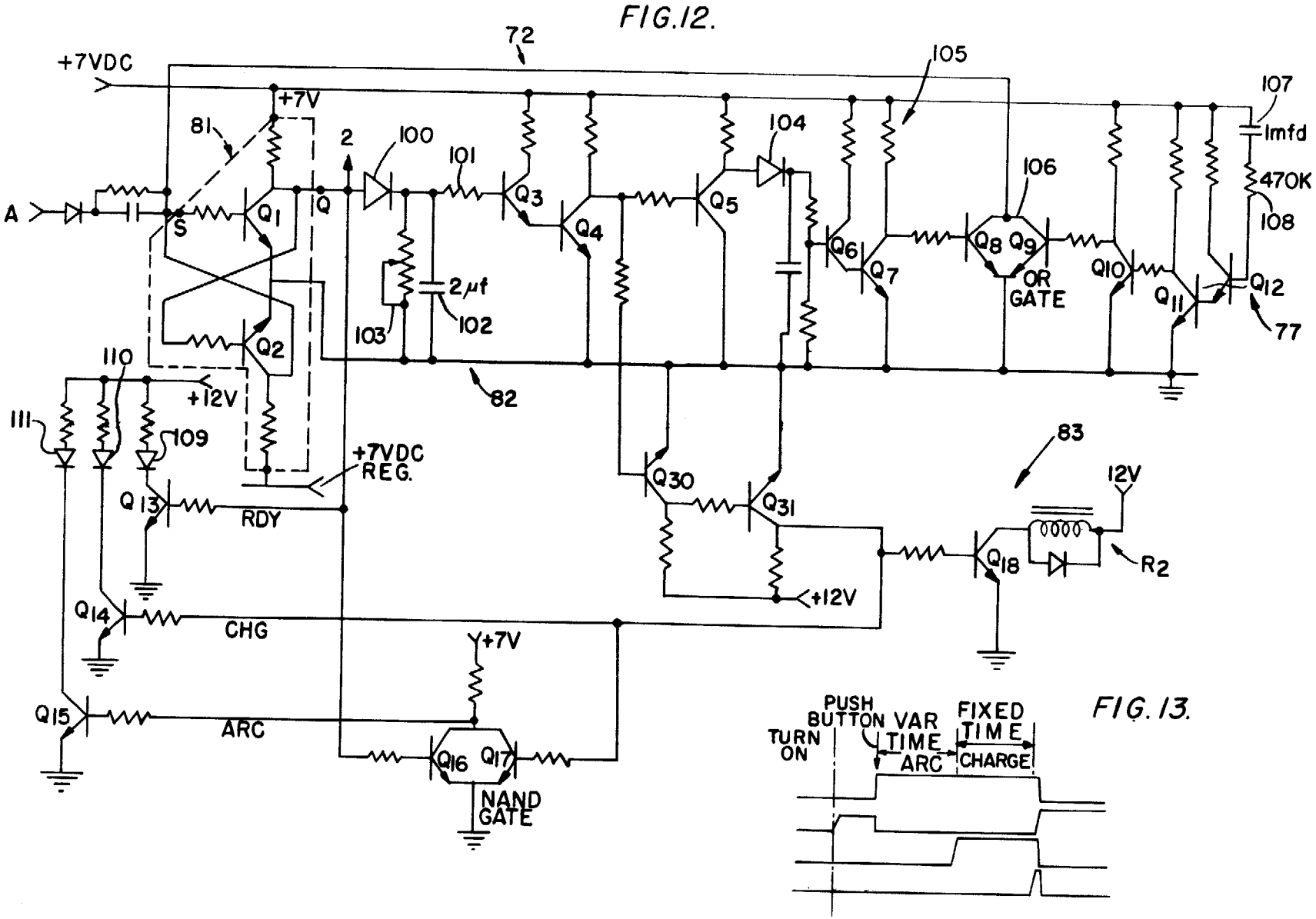
FIG. 12 is a schematic diagram of the discharge control logic circuit.
FIG. 13 is a schematic diagram or chart of the pulse relationships of the various portions of the circuit.

In FIG. 12 input A from the start button or switch 78 located in FIG. 10 is supplied to the set-reset flip-flop 81 comprised of transistors Q1 and Q2. Upon actuation of the start, the transistor Q1 is turned on, setting the flip-flop. The diode, resistor and capacitor on the input is a decoupling diode and a differentiator to generate one pulse to set the flip-flop. When the flip-flop is set, the output of Q1 is coupled through a decoupling diode 100 to the time delay switch circuit 82, which is comprised of transistors Q3 and Q4, Q3 being emitter-coupled to the base of Q4. The time constant is a one megohm series resistor 101 to Q3 and a two microfarad shunt capacitor 102 to ground, which is shunted by a variable one megohm resistor 103. The two microfarad capacitor 102 was previously charged to logic level when the flip-flop went to the set position and discharges when the threshold of the transistor Q3 has been reached. The output of the time circuit then goes low, which drives an inverter Q5 to invert the logic level to a diode decoupling circuit 104 into a second timer 105. The second timer is comprised of transistors Q6 and Q7 and functions similarly to the first timer 82. The output of the second timer 105 is driven into a two input OR gate 106, inverted and used to reset the first set-reset flip-flop 81 and the output of this set-reset flip-flop is used to reset the first start-stop flip-flop 79. The switch 83 is connected with the output of timer 82, and this output is coupled into an inverter and driver transistor Q30 driving a driver transistor Q31, which drives a relay driver transistor Q18, which operates relay No. 2, which operates from 12 volts dc.

The first timer 82, including transistors Q3 and Q4, times the duration of the arc. At the end of the arc duration, transistors Q30 and Q31 and Q18 relay driver are operated, and relay R2 is pulled in, which drops out main power supply relay R1. The emitter-coupler time delay 77 in the logic circuit includes transistors Q11 and Q12, and this time delay is timed by the time constant of a one microfarad capacitor 107 and 470 K resistor 108. This timer is used only upon turning power on to the unit, and is a lockout timer to lock out any erroneous trigger pulses. The output of this timer is inverted by transistor Q10 and fed into the two input OR gate comprising transistors Q8 and Q9.

Status indicators comprising LEDs 109, 110 and 111 are connected with the logic circuit to indicate the status of the device. A transistor Q13 drives the ready LED, which is green. Transistor Q14 drives the amber indicator, which indicates the charge cycle, and transistor Q15 drives the red LED, which indicates the arc cycle. The arc cycle LED is energized from a two input NAND gate comprising transistors Q16 and Q17, which produces a signal inverted from the ready and the charge cycles.

While a specific circuit and housing construction for the beak remover of the invention have been specifically described and illustrated herein, it is to be understood that other circuits capable of performing the necessary function as set forth hereinabove could be used, and the housing need not have the specific shape and structure as shown, so long as the functions and results sought to be obtained by applicant are obtained.

In summation, it should be noted that with the beak remover of the present invention, an initial high voltage spark is caused to be generated across a spark discharge gap when the beak of a bird is inserted into proximity therewith, closing a switch, and this initial high voltage spark is discharged for a prescribed short time to ionize the air in the spark discharge path, and thereafter the high voltage supply is turned off or dropped out and a lower voltage spark discharge is then enabled to jump the spark gap and is used to perform burning of the beak. This is more economical than if the high voltage spark discharge were utilized throughout the debeaking cycle, since smaller power supplies are required and also the life of the electrodes and other components are extended.

As this invention may be embodied in several forms without departing from the spirit or essential characteristics thereof, the present embodiment is, therefore, illustrative and not restrictive, since the scope of the invention is defined by the appended claims rather than by the description preceding them, and all changes that fall within the metes and bounds of the claims or that form their functional as well as conjointly cooperative equivalents are, therefore, intended to be embraced by those claims.

We claim:

1. A poultry beak remover for debeaking fowl, comprising: a housing having a beak receiving aperture therein of a size to receive the beak of a fowl, for insertion of the beak of a fowl into the housing; a pair of spaced apart electrodes supported in the housing in substantial alignment with the aperture and spaced therefrom a distance such that when the beak is inserted through the aperture, a portion thereof extends between the electrodes; and electrical circuit means connected with the electrodes for discharging a spark across the electrodes to burn the beak of the fowl received therebetween and thus effect removal of a desired portion of the beak.

2. A beak remover as in claim 1, wherein means for adjusting the electrodes are connected therewith for adjusting the electrodes relative to the aperture for accommodating fowl of different size, type and the like.

3. A beak remover as in claim 2, wherein a removable mask is releasably secured to the housing and the beak receiving aperture is formed therethrough, whereby masks having different size and shape apertures therethrough can be readily placed on the housing for use with different size and type of fowl and the like.

4. A beak remover as in claim 3, wherein the housing and mask comprise non-conductive material.

5. A beak remover as in claim 2, wherein the means for adjusting the electrodes is adjustable in three directions, whereby the electrodes are adjustable in three directions, and said adjusting means includes a pair of substantially parallel, horizontally extending guide members, a pair of guide sleeves slidably supported on said guide members, a base plate carried by the sleeves for sliding movement in a first horizontal direction, an electrode support means carried by the plate and including means for vertical adjustment of electrodes carried thereby, and electrode attaching brackets carried by the electrode support means supporting the electrodes thereon and adjustable in a second horizontal direction.

6. A beak remover as in claim 1, wherein a switch means is connected with the electrical circuit means and is supported within the housing adjacent the electrodes and in substantial alignment with the aperture and spaced from the aperture a distance to be engaged by the beak of a fowl inserted through the aperture, whereby when the beak of the fowl is inserted through the aperture and between the electrodes, it engages the switch means to close the contacts thereof and thereby energize the electrical circuitry to cause a spark to be discharged across the electrodes.

7. A beak remover as in claim 6, wherein the electrical circuit means includes capacitive discharge circuit means connected with the electrodes for discharge across the electrodes to create a spark to burn the beak of the fowl.

8. A beak remover as in claim 7, wherein the electrical circuit means further includes control circuit means connected with the capacitive discharge circuit means for controlling charge and discharge thereof, said control circuit means including timers to time the duration of the spark.

9. A beak remover as in claim 8, wherein the electrical circuit means further includes lockout time delay circuit means connected with the control circuit means and operative when power is turned on to the debeaker to prevent transient signals and spurious pulses from initiating spark discharge.

10. A beak remover as in claim 8, wherein the electrical circuit means further includes a step-up transformer connected to one of the electrodes and an SCR controlled capacitive discharge circuit means connected with the step-up transformer for initially producing a high potential difference across the electrodes to ionize the spark discharge path.

11. A beak remover as in claim 8, wherein the capacitive discharge circuit means includes a bank of series connected capacitors connected across the electrodes, a high voltage spark induction transformer connected to one of the electrodes, an SCR controlled capacitive discharge circuit means connected with the transformer for producing a high potential difference across the electrodes when the SCR controlled capacitive discharge circuit means discharges, and a tap at one of the capacitors in the bank of capacitors connected with the SCR controlled capacitive discharge circuit means to charge the SCR controlled capacitive discharge circuit means, a power supply, main power supply leads connected with the power supply and with the electrical circuit means, switch means connected in the main power supply leads, relay means connected with the switch means to disconnect the contacts of the switch means, and timer means connected with the relay means to disconnect the power supply at the end of an arc period.

12. A beak remover as in claim 1, wherein means is connected with the housing for producing a vacuum therein to remove noxious odors and aid in holding the beak of the fowl in proper position.

13. A beak remover as in claim 1, wherein the electrical circuit means includes a transistor logic circuit means to control the duration and intensity of the spark and a capacitive discharge circuit connected with the transistor logic circuit means and controlled thereby, said transistor logic circuit means including timer means to control the charge and discharge of the capacitors, and status indicating means connected with the electrical circuit means to indicate when the capacitors are being charged and discharged and to indicate when the electrical circuit means is in a ready state.

*14. Apparatus for burning the beak of a fowl to effect the removal of a portion thereof comprising:*

*mask means having an aperture therein for receiving the face of a fowl with its beak extending through the aperture;*

*a pair of spaced electrodes disposed in alignment with the aperture so that a portion of the beak extending through the aperture is positioned between the electrodes; and,*

*electrical circuit means connected to said electrodes for selectively initiating flow of electric current between said electrodes which burns the beak of a fowl received by said mask means.*

*15. The apparatus of claim 14 wherein said electrical circuit means includes timing circuit means for initiating and maintaining said electric current flow for a predetermined period of time.*

* * * * *